United States Patent
Berryman

(10) Patent No.: US 6,755,083 B2
(45) Date of Patent: Jun. 29, 2004

(54) METHOD FOR DISTINGUISHING MULTIPLE TARGETS USING TIME-REVERSAL ACOUSTICS

(75) Inventor: James G. Berryman, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 82 days.

(21) Appl. No.: 10/131,391

(22) Filed: Apr. 22, 2002

(65) Prior Publication Data

US 2003/0005770 A1 Jan. 9, 2003

Related U.S. Application Data

(60) Provisional application No. 60/298,600, filed on Jun. 13, 2001.

(51) Int. Cl.$^7$ ............................ G01N 29/06; G01N 29/14
(52) U.S. Cl. ............................................ 73/602; 73/628
(58) Field of Search ......................... 73/602, 627, 628, 73/597, 598

(56) References Cited

U.S. PATENT DOCUMENTS

| | | | | |
|---|---|---|---|---|
| 5,092,336 A | * | 3/1992 | Fink | 600/443 |
| 5,428,999 A | * | 7/1995 | Fink | 73/599 |
| 5,431,053 A | * | 7/1995 | Fink | 73/602 |
| 6,161,434 A | * | 12/2000 | Fink et al. | 73/587 |
| 6,202,489 B1 | * | 3/2001 | Beffy et al. | 73/628 |
| 6,490,469 B2 | * | 12/2002 | Candy | 600/407 |

* cited by examiner

*Primary Examiner*—Hezron Williams
*Assistant Examiner*—Rose M. Miller
(74) *Attorney, Agent, or Firm*—Eddie E. Scott; L. E. Carnahan; Alan H. Thompson

(57) ABSTRACT

A method for distinguishing multiple targets using time-reversal acoustics. Time-reversal acoustics uses an iterative process to determine the optimum signal for locating a strongly reflecting target in a cluttered environment. An acoustic array sends a signal into a medium, and then receives the returned/reflected signal. This returned/reflected signal is then time-reversed and sent back into the medium again, and again, until the signal being sent and received is no longer changing. At that point, the array has isolated the largest eigenvalue/eigenvector combination and has effectively determined the location of a single target in the medium (the one that is most strongly reflecting). After the largest eigenvalue/eigenvector combination has been determined, to determine the location of other targets, instead of sending back the same signals, the method sends back these time reversed signals, but half of them will also be reversed in sign. There are various possibilities for choosing which half to do sign reversal. The most obvious choice is to reverse every other one in a linear array, or as in a checkerboard pattern in 2D. Then, a new send/receive, send-time reversed/receive iteration can proceed. Often, the first iteration in this sequence will be close to the desired signal from a second target. In some cases, orthogonalization procedures must be implemented to assure the returned signals are in fact orthogonal to the first eigenvector found.

21 Claims, No Drawings

METHOD FOR DISTINGUISHING MULTIPLE TARGETS USING TIME-REVERSAL ACOUSTICS

RELATED APPLICATION

This application relates to U.S. Provisional Application No. 60/298,600 filed Jun. 13, 2001, and claims priority thereof.

The United States Government has rights in this invention pursuant to Contract No. W-7405-ENG-48 between the United States Department of Energy and the University of California for the operation of Lawrence Livermore National Laboratory.

BACKGROUND OF THE INVENTION

Component parts, whether they are lenses for optical systems or components of sensitive weapon systems, must be inspected regularly as part of a scheduled maintenance and monitoring program, especially during the assembly process. These inspections are critical, because even minute defects can propagate into still larger flaws that lead to a malfunction or possible catastrophic destruction of the system. Most materials, especially in optical components, have many small defects that are distributed throughout; therefore, it is important to select the largest defects that create the strongest returns. A nondestructive evaluation (NDE) technique would be of considerable value for inspecting optics in advanced laser systems and component parts for stockpile stewardship, for noninvasive medical treatments, and for locating underground targets.

A project is underway at the Lawrence Livermore National Laboratory for developing an NDE technique for dynamically focusing acoustical energy for both detecting and characterizing flaws in parts undergoing ultrasonic testing. This project applies a systematic approach that incorporates detailed simulations, algorithm development, hardware, proof-of-principle NDE experiments, and the design of a flaw-detection/localization/imaging system.

The effort enables one or a few strongly scattering targets or defects to be selected from a larger group while the larger group is itself imbedded in a cluttered environment. Current methods for attacking this problem use a time-domain method (which is quite fast) to locate the strongest scatterer or defect reliably. But, in order to distinguish other scatterers or defects, the existing methods require transformation of the data into the frequency domain, and then a difficult procedure (singular value decomposition) is followed to find the eigenvectors and eigenvalues of a complex matrix in the frequency domain. There is clearly a need to design a method that works wholly in the time domain, and is purely empirical, as is the step that determines the location of the first (and strongest) scatterer, defect or target.

The present invention provides a solution to the above referenced problem and involves a method of time-reversal acoustics which uses an iterative process to determine the optimum signal for locating a strongly reflecting target or scatterer in a cluttered environment, similar to the prior techniques, to determine locations of other targets. The present invention provides a means of localizing other targets in the time domain by using properties of constructive and destructive interference of the sound waves. In this method, after locating the stronger (larger) scattering target, instead of sending back the same signals, which are the time-reversed signals, half of the signals will additionally be reversed in sign and, a new send/receive, send-time-reversal/receive iteration process can then proceed with confidence that the stronger (larger) scatterer is no longer contributing to the received signal.

SUMMARY OF THE INVENTION

It is an object of the present invention to distinguish multiple targets using time-reversal acoustics.

A further object of the invention is to provide a method for locating a number of targets imbedded in a cluttered environment in the time domain rather than in the frequency domain.

A further object of the invention is to provide a method for locating different targets by time-reversal acoustics using an interative process which operates in the time domain.

Another object of the invention is to provide a method for sequentially locating targets of smaller size or scattering strength using the time domain, wherein after locating a larger target, instead of sending back the same signals, which are time reversed signals, the method sends back these signals but with half of them reversed in sign.

Another object of the invention is to enable localizing smaller or more distant targets in the time domain by using properties of constructive and destructive interference of the sound waves by reversing in sign half of the time-reversed signals.

Other objects and advantages of the present invention will become apparent from the following description. The invention involves distinguishing multiple targets using time-reversal acoustics. The invention enables localizing both the larger (stronger) and smaller (weaker) targets in the time domain, thereby eliminating the prior problems of locating the smaller (weaker) targets using the frequency domain of the prior known techniques. In the present invention, after the locating a strongly reflecting target in a cluttered environment using the conventional or standard time-reversal acoustics, the invention provides for localizing other targets in the time domain by using properties of constructive and destructive interference of the secondary waves. After the largest eigenvalue/eigenvector combination has been determined, instead of sending back the same time-reversed signals, half of the signals are reversed in sign. There are various ways of choosing which half of the signals to reverse. One choice is to reverse every other signal in a linear array, or as in a checkerboard pattern for a 2D array of transducers. These reversing signal choices are made to enhance the likelihood that the signal received at the strongest scatterer is weak due to destructive interference of the arrivals. Then, a new send/receive, send-time-reversed/receive iteration can proceed with confidence that the largest (strongest) scatterer is no longer contributing to the received signal. Many choices of the pattern of sign reversal of the signals may be constructed. Discrete analogs of sines and cosines along the array provide one class of choices. After the second strongest (smallest) scatterer or target has been located using this method, then the procedure can be repeated always in time domain using known sequential orthogonalization techniques. Often, the first iteration in this sequence will be close to the desired signal from a second target. In some cases, orthogonalization procedures must be implemented to assure the returned signals are in fact orthogonal to the first eigenvector found.

DETAILED DESCRIPTION OF THE INVENTION

The present invention is directed to distinguish multiple targets using time-reversal acoustics. The invention enables the localization of targets or scatterers of varying sizes or strengths in the time domain thereby eliminating problems associated with the prior known technique that involves heavy use of the frequency domain. The time-reversal acoustics of the present invention uses an iterative process to determine the optimum signal for locating a strongly reflecting target in a cluttered environment, as in the prior known techniques. To determine locations of other targets, the invention provides a means of localizing other targets in the time domain by using properties of constructive and destructive interference of the sound waves. After the largest eigenvalue/eigenvector combination has been determined in the standard method, instead of sending back the same signals, the method of the invention will send back these time reversed signals, but half of them will be reversed in sign. After a second scatterer has been located using this method, then the procedure can be repeated always in the time domain using known sequential orthogonalization techniques.

The principle object of the present invention is to permit one or a few strongly scattering targets to be selected from a larger group while the larger group is itself imbedded in a cluttered environment.

As pointed out above, time-reversal acoustics uses an iterative process to determine the optimum signal for locating a strongly reflecting target in a cluttered environment. An acoustic array sends a signal into the medium, and then receives the returned/reflected signal. This signal is then time-reversed and sent back into the medium again, and again, until the signal being sent and received is no longer changing. At that point, the array has isolated the largest eigenvalue/eigenvector combination and has effectively determined the location of a single target in the medium (the one that is most strongly reflecting). Strictly speaking, it has not located the object or target, but only located a set of unknown acoustic paths that converge on and constructively interfere at the surface of the strongest scatterer; these constructively interfering signals are then reflected back to the source array. It is well-understood that the resulting method is an example of the power method for finding the largest eigenvalue/eigenvector of any system of equations; the largest eigenvalue is usually unique, and the others fall off in this process according to a power law, to the power of the number of iterations used. If the eigenvalues are well-separated, which is usually the case, this method converges rapidly. The method has the great advantage that relatively little processing of the data is required, since everything is taking place in the time domain.

To determine locations of other targets (besides the strongest scatterer), existing techniques then, as pointed out above, pursue a rather different strategy in the frequency domain. The present invention provides a method of localizing other targets in the time domain by using properties of constructive and destructive interference of the sound waves. After the largest eigenvalue/eigenvector combination has been determined using the standard method, instead of sending back the same signals, the present invention will also send back the time-reversed signals, but half of them will additionally be reversed in sign. Various possibilities for choosing which half to reverse exist. The most obvious choice is to reverse every other one in a linear array, or as in a checkerboard pattern for a 2D array of transducers. These choices are made to enhance the likelihood that the signal received at the strongest scatterer is weak due to destructive interference of the arrivals. Then, a new send/receive, send-time-reversed/receive iteration process can proceed with confidence that the largest scatterer is no longer contributing to the received return signal. It is possible to construct many choices of the pattern of sign reversal. Discrete analogs of sines and cosines along the array provide one class of such choices. After a second scatterer has been located using this method, then the procedure can be repeated always in the time domain using known sequential orthogonalization techniques.

To provide an example of a type of excitation scheme of the invention, consider a linear array having eight transducers. After the initial send/receive sequence, there are eight returned signals $Si(t)$, for $i=1, 2, 3, \ldots, 8$. These signals will normally be time-reversed $Si(-t)$, and then rebroadcast. This case is symbolized by the vector (11111111). The ones here stand for the prefactor in front of the signal function $Si(-t)$, which is unity in all cases for the standard time-reversal acoustics using an iterative process. Now this procedure is modified to send instead a signal $AiSi(-t)$, where the $Ai$'s are given by the components of a vector of the form (A1 A2 A3 A4 A5 A6 A7 A8). Seven interesting and useful choices of this vector are listed in Table I.

TABLE I

| (1 | −1 | 1 | −1 | 1 | −1 | 1 | −1) |
|---|---|---|---|---|---|---|---|
| (1 | 1 | −1 | −1 | 1 | 1 | −1 | −1) |
| (1 | 1 | 1 | 1 | −1 | −1 | −1 | −1) |
| (−1 | 1 | 1 | −1 | 1 | −1 | −1 | 1) |
| (−1 | 1 | −1 | 1 | 1 | −1 | 1 | −1) |
| (−1 | −1 | 1 | 1 | 1 | 1 | −1 | −1) |
| (−1 | 1 | 1 | −1 | −1 | 1 | 1 | −1) |

These seven choices of Table I are all orthogonal to the first case with all ones, and they are also all mutually orthogonal. These choices can be viewed as discrete analogs of the sine and cosine functions, which are well-known to be mutually orthogonal, as well as being orthogonal to a constant.

Any of these choices could be used as the starting point of a new time-reversal iteration sequence. Each of them will produce a result that is certainly destructively interfering at the location of the strongest scatterer on the first iteration. The result of the iteration process may however not end up being exactly one of these choices; it may instead be a complicated linear combination of them, or something somewhat different if the environment is complex and the scatterers are well separated in distance from the transducer array (for example, the reflected time signals may become significantly longer than those obtained for the first scatterer).

To proceed further and find other targets requires a more complex iteration sequence. Standard methods are available to produce other candidates when two eigenvectors are known. The vectors shown above in Table I can be used to facilitate these methods.

Uses for this invention are many. While the invention has particular utility for biomedical applications, for example, uses of ultrasound to detect and then disintegrate kidney stones, other applications include the location and disarming of both landmines and antisubmarine and antishipping mines in ocean or harbor environments. The method can also be generalized to other types of waves, for example, in wireless communication (using electromagnetic radiation) in a cluttered urban environment, or in ground penetrating radar for landmine detection. It is clearly of importance to be able to locate more than one target in a cluttered environment, otherwise the obvious countermeasure to this type of technique is to place two objects in the environment, one of which is decoy that is also designed to be the largest scatterer.

It has thus been shown that the present invention enables distinguishing multiple targets using time-reversal acoustics and in the time domain, and after establishing a location of the most reflecting or strongest scatterer, the invention enables localizing other targets in the time domain by using properties of constructive and destructive interference of the sound waves.

While particular approaches for carrying out the invention, including specific embodiments and parameters, have been described to exemplify and teach the principles of the invention, such are not intended to be limiting. Modifications and changes may become apparent to those skilled in the art, and it is intended that the invention be limited only by the scope of the appended claims.

What is claimed is:

1. A method for distinguishing a plurality of targets using time-reversal acoustics, comprising:
   providing an acoustic array for sending at least one signal into a medium,
   receiving a returned/reflected signal from the medium,
   time-reversing the returned/reflected signal and sending that signal back into the medium,
   reiterating the sending, receiving, sending process until the signal sent and received is no longer changing whereby the target eigenvalue/eigenvector combination is isolated and a location of a single target in the medium is determined, and
   determining the location of at least one other target in the time domain using properties of constructive and destructive interference of the sound waves.

2. The method of claim 1, wherein using properties of constructive and destructive interference of the sound waves is carried out by:
   sending back to the medium the time-reversed signals, and
   reversing in sign half of these signals.

3. The method of claim 2, additionally including determining which half of the signals to reverse in sign.

4. The method of claim 3, wherein determining which half of the signals to reverse in sign is carried out by reversing every other signal in a linear array.

5. The method of claim 3, wherein determining which half of the signals to reverse in sign is carried out by forming a checkerboard pattern for a 2D array.

6. The method of claim 3, wherein determining which half of the signals to reverse in sign is carried out so as to enhance the likelihood that the signal received at the strongest scatter is weak due to destructive interference of the arrivals.

7. The method of claim 3, wherein determining which half of the signals to reverse in sign is carried out by establishing discrete analogs of sines and cosines along an array of n-numbered transducers.

8. The method of claim 3, wherein determining which half of signals to reverse in sign is carried out by providing a linear array of transducers, and by sending a signal AiSi(−t), where the Ai is given by the components of a vector of the form (A1–An).

9. In a method utilizing time-reversal acoustics and an iterative process to determine the optimum signal for locating a strongly reflecting target in a cluttered environment, the improvement comprising:
   locating a lesser reflecting target in the cluttered environment in a time domain.

10. The improvement of claim 9, wherein locating the lesser reflecting target is carried out using properties of constructive and destructive interference of the sound waves.

11. The improvement of claim 9, wherein locating the lesser reflecting target is carried out using an iteration of time-reversed signals wherein half of the signals are reversed in sign.

12. The improvement of claim 11, additionally including determining which half of the signals is reversed in sign.

13. The improvement of claim 12, wherein determining which half of the signal is reversed in sign is carried out by reversing every other signal in a linear array of transducers or as in a checker-board pattern for a 2D array of transducers.

14. The improvement of claim 12, wherein determining which half of the signal is reversed in sign is carried out using discrete analogs of sines and cosines along an array of transducers.

15. The improvement of claim 9, additionally including locating another reflecting target by repeating the operation for the lesser reflecting target in time domain using sequential orthogonalization techniques.

16. A method for distinguishing multiple targets using time-reversed acoustics which includes:
   providing an array of acoustic transducers,
   isolating a target having the largest eigenvalue/eigenvector combination using an iteration of time-reversed acoustic signals produced by said array of acoustic transducers, and
   determining a location of at least one other target in a time domain,
   wherein the iteration of time-reversed acoustic signals is performed by reiterating a process of alternating sending and receiving of acoustic signals until the signal sent and received is no longer changing.

17. The method of claim 16, wherein determining the location of at least one other target is carried out using properties of constructive and destructive interference of the sound waves.

18. The method of claim 17, wherein the properties of constructive and destructive interference of the sound waves is produced by sending back an interation of time-reversed acoustic signals, wherein half of the signals are reversed in sign.

19. The method of 18, additionally including determining which half of the signals are reversed in sign.

20. The method of claim 16, wherein providing an array of acoustic transducers is carried out by a linear array of eight transducers, wherein isolating the target having the largest eignevalue/eigevector combination is carried out by an initial iteration of send-receive time-reversed signal sequence resulting in eight returned signals Si(−t), and wherein determining the location of the at least one other target in the time domain is carried out by sending modified signals AiSi(−t), where the Ai is given by the components of a vector of the form (A1 A2 A3 A4 A5 A6 A7 A8), which enables seven choices of this vector.

21. The method of claim 20, wherein the seven choices are all orthogonal to the signals Si(−t), and wherein the seven choices are also mutually orthogonal.

* * * * *